United States Patent [19]

Shanbrom

[11] Patent Number: 5,370,869
[45] Date of Patent: Dec. 6, 1994

[54] ANTIMICROBIAL PRESERVATION OF PLATELETS AND BLOOD FACTORS

[76] Inventor: Edward Shanbrom, 2252 Liane La., Santa Ana, Calif. 92705

[21] Appl. No.: 753,813

[22] Filed: Sep. 3, 1991

Related U.S. Application Data

[63] Continuation-in-part of Ser. No. 577,204, Sep. 4, 1990, abandoned, and a continuation-in-part of Ser. No. 577,295, Sep. 4, 1990, abandoned.

[51] Int. Cl.$^5$ .............................................. A61K 31/02
[52] U.S. Cl. ................... 424/78.22; 424/405; 422/28; 422/37
[58] Field of Search ............ 424/405, 473, 78.22; 422/28, 37

[56] References Cited

U.S. PATENT DOCUMENTS

| | | | |
|---|---|---|---|
| 2,739,922 | 3/1957 | Shelanski | 422/28 |
| 3,216,579 | 11/1965 | Shelanski et al. | 422/28 |
| 3,907,720 | 9/1975 | Field et al. | 422/28 |
| 4,017,407 | 4/1977 | Cantor et al. | 422/28 |
| 4,898,572 | 2/1990 | Surugue nee Lasnier | 422/28 |
| 4,959,310 | 9/1990 | Selnick et al. | 422/28 |
| 4,971,760 | 11/1990 | Rubinstein | 422/28 |
| 4,976,969 | 12/1990 | Plamondon | 422/28 |
| 5,071,648 | 12/1991 | Rosenblatt | 424/78.26 |
| 5,185,371 | 2/1993 | Rubinstein | 422/28 |

OTHER PUBLICATIONS

Abdullah, M. E., et al., *Influence of Biological Fluids on the Release of $^{125}I$ from Povidone–Iodine*, Arzneim.-Forsch./Drug Res. 31 (I), Nr. 5, 1981.

Anderson, R. L., et al *Microbiological Investigations with Iodophor Solutions*, pp. 146–157, Proc. Int. Symp. on Providone, Int. Symp. on Povidone, 1st 1983, College of Pharm., Univ. of Kentucky, Lexington, Ky., USA.

Bond, W. W., et al, *Obs. Sporicidal, Bactericidal and Virucidal Activity of Iodophors*, pp. 167–177, Proc. Int. Symp. on Providone, Int. Symp. on Providone, 1st 1983, College of Pharm., Univ. of Kentucky, Lexington, Ky., USA.

Digenis, G. A. *Studies on the association of $^{14}C$–Povidone-$^{131}I$–Iodine Complex with Red Blood Cells and Bacterial Membranes*, pp. 302–311, Proc. Int. Symp. on Povidone, Int. Symp. on Povidone, 1st 1983, College of Pharm., Univ. of Kentucky, Lexington, Ky., USA.

Farmer, M. D. *Procurement of Deep Tissues and Bones* Navy Tissue Bank, Tissue Bank Coordinator Manual, Naval Hospital, San Diego, California.

Gershenfeld, L. *Povidone–Iodine as a Topical Antiseptic* Am. J. Surg., V 94, Dec. 1957, pp. 938–939.

Goodman, N. L., et al *A preliminary comparative investigation of povidone iodine and tincture of iodine in the killing of selected microorganisms in vitro.*, pp. 526–529, Proc. Int. Symp. on Povidone, Int. Symp. on Povidone, 1st 1983, College of Pharm., Univ. of Kentucky, Lexington, Ky., USA.

Knolle, P. *Risks and Benefits of Povidone (PVP) in Drugs with Special Reference to High–Molecular Weight (K30)PVP in PVP–Iodine*, pp. 370–409, Proc. Int. Symp. on Povidone, Int. Symp. on Povidone, 1st 1983, College of Pharm., Univ. of Kentucky, Lexington, Ky., USA.

Lacey, R. W., *Antibacterial Activity of Povidone Iodine towards Non-sporing Bacteria*, J. App. Bacteriology 1979, 46, 443–449.

Sheikh, W. *Comparative Antibacterial Efficacy of HIBICLENS® and BETADINE® in the Presence of Pus derived from Human Wounds*, Cur. Ther. Res., 40, 6, Dec. 1986, pp. 1096–1102.

(List continued on next page.)

*Primary Examiner*—Thurman K. Page
*Assistant Examiner*—Raj Bawa
*Attorney, Agent, or Firm*—Grant L. Hubbard

[57] ABSTRACT

A method of purifying platelet-bearing liquid by contacting the liquid to be purified with solid povidone-iodine to expose the liquid to $I_2$ on such surface to kill pathogenic organisms therein and removing the liquid from contact with the solid povidone-iodine, and the use of the same in treating patients are disclosed.

10 Claims, No Drawings

OTHER PUBLICATIONS

Shelanski, H. A. and M. V., *PVP–Iodine: History, Toxicity and Therapeutic Use*, J. Int. Col. Surgeons, Jun. 1956, pp. 727–734.

Shelanski, M. V. et al. *Water–Insoluble Polyvinylpyrrolidone Composition*.

van den Broek, P. J. et al. *Interaction between Betadine Solution, Cells and Microorganisms*, Proc. II World Congress Antisepsis, 1980, HP Publishing Co., Inc., N.Y., N.Y., pp. 25–27.

van den Broek, P. J. et al. *Interaction of Povidone–iodine Compounds, Phagocytic Cells, and Microorganisms*, Antimicrobial Agents and Chemotherapy, Oct. 1982, pp. 593–597.

van den Broek, P. J., et al., *Which Concentrations of Povidone–Iodine should be used Clinically?* pp. 334–341, Proc. Int. Symp. on Povidone, Int. Symp. on Povidone, 1st 1983, College of Pharm., Univ. of Kentucky, Lexington, Ky., USA.

Zamora, J. L., et al. *Inhibition of povidone–iodine's bactericidal activity by common organic substances: An experimental study*, Surgery, Jul. 1985, pp. 25–29.

ANTIMICROBIAL PRESERVATION OF PLATELETS AND BLOOD FACTORS

CROSS-REFERENCE TO RELATED APPLICATIONS

This is a continuation-in-part of my copending patent applications Ser. Nos. 577,204 and 577,295 both filed Sep. 4, 1990, both now abandoned.

FIELD OF THE INVENTION

This invention relates to the treatment and preservation of platelets. More specifically, this invention relates to the treatment of platelets and blood factors to kill or inactivate virus, bacteria, chlamydia, rickettsia, mycoplasma and other potentially pathogenic microorganisms, and to retain the viability of platelets and blood factors.

BACKGROUND OF THE INVENTION

Definitions The following terms, which are used throughout the specification, will be used and understood to have the meaning stated unless another or different meaning is specified or clear from the context.

Donor. While the term "donor" is not usually applied to the individual from whom such samples are acquired, that term, "donor" will be used here in a more general sense to include the individual from who any blood, tissue, cells or fluid is obtained for any purpose, and such term will be used to refer even to an unwilling donor.

Blood. The term "blood" means whole blood and blood fractions, components, and products of blood, unless "whole blood" or a specific blood fraction, component or product of blood is stated.

Povidone (USP) is used in the sense that it is used in the U.S. Pharmacopeia to describe grades of polyvinyl pyrrolidone (PVP) suitable for introduction into the human body.

GTPD triterpenoid compounds derived glycyrrhiza glabra or analogous to such compounds, the most important of which are carbenoxolone and glycyrrhizin.

Blood products such as platelet concentrates carry with them the risk of infecting the recipient with any of an number of diseases. CMV and EBV being very commonly found in such concentrates and HIV and hepititis virus being the most feared. Another organism which is frequently present in blood and blood products or fractions and which presents a serious risk in certain procedures is the bacteria *Yersinia enterocolitica* which is become a serious contaminant, surpassing Salmonella and Campylobacter as a cause of acute bacterial gastroenteritis. A significant increase in transfusion related infections of *Y. enterocolitica* has been reported, Tipple, et al., Transfusion 30, 3, p.207 (1990). *Y. enterocolitica* and other bacteria which propagate at relatively low temperatures, e.g. *Staphylococcus epidermidis* and *Legionella pneumophila*, present, potentially, a serious threat in blood products.

Bacterial infections, generally, are a continuing concern to blood bankers and those who produce transfusion products from blood. Indeed, a national surveillance system for transfusion-associated bacterial infections has been called for, Editorial, Transfusion 30, 3, p. 193 (1990).

In addition to the risk of transmitting infectious disease via blood or blood products, the growth of bacteria in blood and blood products at various stages of production and processing introduces pyrogens into the blood component or product which must be removed before the product can be used in therapy. Introduction of molecular iodine, e.g. povidone-$I_2$, at an early stage in processing of blood products greatly reduces or elinfinates the pyrogen-load of the ultimate product or fraction.

Protozoa give rise to many diseases, some of great medical and economic importance. Examples of such protozoa are the genus Plasmodium, e.g. *P. falciparum, P. malariae, P. ovale* and *P. vivax*, which causes malaria, Trypanosoma, which causes Chagas' disease, and Leishmania, which cause a variety of leishmaniasis. The method of this invention is effective in eliminating these causative organisms in blood and blood products.

Generally, this invention is applicable to the treatment of donated blood and products produced from blood, tissues and fluids for inactivating virus, bacteria, chlamydia, rickettsia, mycoplasma and other potentially pathogenic microorganisms.

Among the important potential pathogens to which this invention is applicable is cytomegalovirus (CMV), probably the most ubiquitous of the pathogenic microorganisms found in animal fluids and tissues. CMV is frequently associated with, and may be a causative or contributing factor in, life threatening disease in individuals with suppressed immune systems, and can be a principal causative factor in pneumonia, neurological disorders, febrile illness, ocular disease and hepatitis. CMV infection is a serious limiting factor in the transplantation of organs, tissues and cells and the transfusion of blood and plasma from one individual to another. The kidney transplant patient runs a high risk of contracting serious, and not infrequently fatal, CMV infection from CMV introduced by the transplant organ. Recipients of whole blood, plasma, bone marrow, cornea, cardiac, and semen run a serious risk of CMV infectious disease, the risk being multiplied where the immune system of the recipient is suppressed to prevent rejection of the foreign organ or cells, or where immunosuppression is present from natural causes.

This invention has application in preventing the transmission of herpesviruses generally. Herpesviruses, of which CMV is a member, represent a very large group of viruses which are responsible for, or involved in, cold sores, shingles, a venereal disease, mononucleosis, eye infections, birth defects and probably several cancers. Three subfamilies are of particular importance. The alpha subfamily includes HV 1 (herpes virus simplex 1) which causes cold sores, fever blisters, eye and brain infections, HV 2 (herpes virus simplex 2) which cause genital ulceration, and HV 3 (HV varicella zoster) which causes chicken pox, shingles and brain infections. The beta subfamily includes HV 5, the principal member of which is CMV discussed above. The gamma subfamily includes HV 4 (Epstein-Barr) which cause infectious mononucleosis and is involved in Burkitt's lymphoma and nasopharyngeal carcinoma.

The present invention is also useful in preventing the transmission of human immunodeficiency virus (HIV). While testing has made blood products safer than it was a decade ago, the complete elimination of HIV contaminated blood and blood products has not been possible using present knowledge and technology.

It is apparent from the foregoing discussion that a method of killing or inactivating pathogenic viruses in organs, tissues, cell and fluids intended for transfusion or transplantation would be an enormous advance in medicine. It is to this major national and worldwide health care challenge that the present invention is directed.

My U.S. Pat. No. 4,891,221 describes and claims a method for inactivating virus in blood samples using glycyrrhizic triterpenoid compounds. While the use of glycyrrhizic triterpenoid compounds in blood product treatment is a major step forward, there remains a need for a method of treatment which would kill or inactivate all or nearly all pathogenic organisms, including those in the cells of the blood or blood products.

Other diseases which can be transmitted from the donor(s) to the patient(s) include the numerous diseases in which the causative pathogen appears in viable form, at least during one stage of development, in the blood, fluids or tissues of the donor. The risk can be reduced by screening potential donors and refusing to accept blood, tissue or fluids for transfer to patients; however, the availability of blood, blood fractions and products, tissues and fluids could be very greatly increased and the cost thereof greatly decreased if all potential donors could be accepted followed by killing all potential pathogens in the donated blood, fluid or tissue.

The use of elemental iodine as an antiseptic dates back to 1839. It is used today for various medicinal purposes. The combination of iodine with various solubilizing polymers led to a class of new compositions known as iodophors, which dominate the market once satisfied by simple alcoholic or aqueous iodine solutions. The iodine complexes with either nonionic surfactants, e.g., polyethylene glycol mono(nonylphenyl) ether, or poly(vinylpyrrolidone) (PVP). The complexes function by rapidly liberating free iodine in water solutions. They exhibit good activity against bacteria, molds, yeasts, protozoa, and many viruses; indeed, of all antiseptic preparations, only povidone-iodine is capable of killing all classes of pathogens encountered in nosocomial infections: gram-positive and gram-negative bacteria, mycobacteria, fungi, yeasts, viruses and protozoa. Most bacteria are killed with 15 to 30 seconds of contact. These iodophors are generally nontoxic, nonirritating, non-sensitizing, and noncorrosive to most metals (except silver and iron alloys). Medicinal povidone-iodine preparations include aerosol sprays, gauze pads, lubricating gels, creams, solutions, douche preparations, suppositories, gargles, perineal wash solutions, shampoos, and skin cleansers and scrubs. Povidone-iodine preparation are applied topically to the skin and to membranes, e.g. vaginal membranes, and in infected wounds and surgical incisions.

The uses continue to be largely medicinal, though some iodophors are used in industrial sanitation and disinfection in hospitals, building maintenance, and food-processing operations. There has been some interest in the use of iodine for purification of potable water and swimming pools. Two other iodine-containing compounds, p-tolyl diiodomethyl sulfone and p-chlorophenyldiiodomethyl sulfone have been recommended as preservatives.

Iodine and iodine-containing compounds and preparations are employed extensively in medicine, e.g., as antiseptics, as drugs administered in different combinations in the prophylaxis and treatment of certain diseases, and as therapeutic agents in various thyroid dyscrasias and other abnormalities. Iodine is a highly reactive substance combining with proteins partly by chemical reaction and partly by adsorption. Therefore its antimicrobial action is subject to substantial impairment in the presence of organic matter such as serum, blood, urine, milk, etc. However, where there is no such interference, non-selective microbicidal action is intense and rapid. A saturated aqueous solution of iodine exhibits anti-bacterial properties. However, owing to the low solubility of iodine in water (33 mg/100 Ml at 25° C.), reaction with bacteria or with extraneous organic matter rapidly depletes the solution of its active content. Iodide ion is often added to increase solubility of iodine in water. This increase takes place by the formation of triiodide, $I_2 + I^- = I3^-$. An aqueous solution of iodine and iodide at a Ph of less than 8 contains mainly free diatomic iodine $I_2$ and the triiodide $I3^-$. The ratio of $I_2$ and $I_3$ depends upon the concentration of iodide.

An important solubilizing agent and carrier for iodine is polyvinyl pyrrolidone (PVP), one grade of which is identified as povidone USP. Povidone-iodine (PVP-iodine), is widely used externally on humans as an antiseptic. Such products are marketed as Betadine TM and Isodine TM by The Purdue-Frederick Co.). Povidone-iodine products and the preparation of such products are described in U.S. Pat. Nos. 2,707,701, 2,826,532, and 2,900,305 to Hosmer and Siggia, assigned to GAF Corporation and in a number of GAF Corporation publications; see, e.g. Tableting with Providone¾ povidone USP (1981) and PVP Polyvinylpyrrolidone (1982). Povidone-iodine powder contains approximately 85% PVP, 10% $I_2$ and 5% Iodide. A 10% solution of this powder contains 1% free, available iodine. (Gershenfeld, Am. J. Surgery 94, 938 (1957)).

Under ordinary conditions, PVP is stable as a solid and in solution. The single most attractive property of PVP is its binding capability. This property has permitted utilization in numerous commercial applications. Small quantities of PVP stabilize aqueous emulsions (qv) and suspensions, apparently by its absorption as a thin layer on the surface of individual colloidal particles. The single most widely studied and best characterized PVP complex is that of PVP-iodine. For example, hydrogen triiodide forms a complex with PVP that is so stable that there is no appreciable vapor pressure. It is superior to tincture of iodine as a germicide.

Although iodine is less likely to be consumed by proteinaceous substrates than bromine and chlorine, its efficacy as a disinfectant is still reduced at certain antiseptic applications. This is due to a reducing effect of the material to be disinfected which leads to the conversion of iodine into non-bactericidal iodide. Thus, not only the reservoir of available iodine is diminished but also the equilibrium of triiodide is influenced as well. Both of these effects cause a decrease in the proportion of free molecular iodine, the actual anti-microbial agent. When povidone-iodine preparations are contaminated with liquid substrata (e.g. blood, etc.) there is, in addition. the dilution effect characteristic of povidone-iodine systems which causes an increase in the equilibrium concentration of free molecular iodine. To what extent the latter effect compensates for the other two effects depends on the content of reducing substances. Thus with full blood, a strong decrease of the concentration of free molecular iodine occurs, while, in the presence of plasma, it remains practically unchanged. Durmaz, et al, Mikrobiyol. Bul. 22 (3), 1988 (abstract); Gottardi W, Hyg. Med. 12 (4). 1987. 150–154. Nutrient broth and plasma had little inactivating activity but 1 g hemoglobin inactivated 50 mg of free I; experiments with $^{125}I$ showed that uptake of I by [human] red cells occurred rapidly. Optimal antimicrobial effects in clinical use should be achieved in relatively blood-free situations. Povidone iodine produced a potent and sometimes persistent bactericidal effect towards bacteria on healthy skin. Lacey, R. W. J Appl Bacteriol 46 (3). 1979. 443–450. The bactericidal activity of dilute povidone-iodine solutions is inversely proportional to the concentration of the povidone-iodine solutions and is inhibited to the greatest extent by blood, followed by pus, fat and glove powder. Zamora J L; Surgery (St Louis) 98 (1). 1985. 25–29: Zamora, Am. J. Surgery, 151, p. 400 (1986); see also, Waheed Sheikh, Current Therapeutic Research 40, No. 6, 1096 (1986). Van Den Broek, et al, Antimicrobial Agents and Chemotherapy, 1982, 593–597, suggests that povidone-iodine is bound to cell wall proteins leaving little for interaction with microorganisms in the liquid phase (See, also, Abdullah, et al., Arzneim.-Forsch./Drug Res. 31 (I), Nr. 5, 828). Ninneman et al, J. of Immunol. 81, 1265 (1981) reported that povidone-iodine was absorbed in serum albumin and it is know that povidone-iodine is bound to albumin but it has been discovered that the antibiotic activity of povidone-iodine is not destroyed by albumin bounding. Whether the activity remains because the albumin povidone-iodine is active or whether povidone-iodine and/or $I_2$ are released from the albumin-povidone-iodine complex.

The teachings of the prior art suggest that neither elemental (diatomic) iodine nor complexed iodine, e.g. PVP—$I_2$, would be an effective and reliable biocide in a fluid or in a body, e.g. blood, packed or concentrated cells, organs, etc. in which massive amounts of protein are be available to react with the iodine.

SUMMARY OF THE INVENTION

This invention relates to the treatment of platelets treated to inactivate or destroy infective pathogenic microorganisms with molecular iodine, preferably absorbed by or in complex with an organic stabilizer.

This invention is also embodied in a method of treating patients with blood factors, e.g. Factor VIII or Anti-Hemophilia Factor (AHF), to increase the biological half-fife of such factors in therapy, and to compositions of such factors and methods of preparing the same.

The invention relates specifically to the preservation and protection of platelets and blood factors

DESCRIPTION OF THE PREFERRED EMBODIMENT

The invention comprises a method treating patients to prevent the transmission of disease by infusing into the patient a platelet containing liquid that has been in contact with povidone-iodine or povidone-hydrogen peroxide, or a mixture of povidone-iodine and povidone-hydrogen peroxide in a concentration of from 0.001 to 0.5 weight percent for at least one-half minute sufficient to inactivate or destroy infective pathogenic microorganisms therein. Povidone in amounts of up to 5% may be used to advantage; however, the iodine concentration should not exceed about 0.05 percent. Hydrogen peroxide, in the form of povidone hydrogen peroxide complex may be present in lieu of or in addition to povidone iodine in concentrations of up to about 0.1% hydrogen peroxide.

The invention also constitutes a method of protecting platelets comprising storing said platelets in a solution comprising from at least about 0.1 weight percent povidone and thereafter reconstituting the platelets in plasma for infusion into a patient. While the platelets are distinctly abnormal in povidone solution, washing and reconstituting the platelets returns them to a very nearly normal configuration and with normal clotting characteristics. A sterilizing amount of povidone iodine or povidone hydrogen peroxide or triterpenoid compounds derived glycyrrhiza glabra or analogous to such compounds, the most important of which are carbenoxolone and glycyrrhizin may also be used or the platelet carrying solution may be passed over solid povidone iodine to obtain sterilization. Preferably, the solution comprises at least 0.1 weight percent povidone iodine, at least half of the povidone therein having a molecular weight of less than about 40 kD, the preferred molecular weight for at least half the povidone being in the range of 15 kD.

The invention also includes the method of purifying platelet-bearing liquid comprising contacting the liquid to be purified into contact with solid povidone-iodine having sufficient surface area to expose the liquid to sufficient $I_2$ on such surface to kill pathogenic organisms therein removing the liquid from contact with the solid povidone-iodine. The method include the step of reacting the surface of the solid povidone-iodine with iodine and/or hydrogen peroxide to regenerate the iodine content thereof.

The method of treating patients comprising infusing into the blood stream of the patient an aqueous solution consisting essentially of one or more blood factors and povidone or albumin or a mixture of povidone or albumin is also a facet of the invention. Such solutions may optionally comprise a povidone-iodine complex wherein the ratio of povidone to iodine is at least about 12 to 1, preferably between 15 to 1 and 60 to 1. Another facet of the invention is embodied in a composition consisting essentially of one or more human blood factors free from significant quantities of blood plasma and povidone or albumin or a mixture of povidone and albumin and optionally povidone-iodine complex wherein the ratio of povidone to iodine is at least about 15 to 1. The invention is also embodied in a method of preparing human blood factors for infusion into a patient comprising mixing one or more blood factors that are substantially free from blood plasma with one or more blood factors and povidone or albumin or a mixture of povidone or albumin and optionally with povidone-iodine complex wherein the ratio of povidone to iodine is at least about 12 to 1.

In a general sense, one facet of this invention relates to the treatment of platelets to inactivate or destroy infective extracellular and intracellular pathogenic microorganisms with molecular iodine, preferably absorbed by or in complex with an organic stabilizer.

Blood plasma may be treated in accordance with this invention by introducing molecular iodine, e.g. povidone-$I_2$, into the plasma to produce a concentration of from about 0.01 to about 0.5 wt % in the plasma. Concentrations in the range of about 0.1 to 0.25 are presently considered most suitable. It is known, for example, that a 0.25 wt % concentration of $I_2$ in plasma provides a total kill of bacteria and virus. This has the effect of preserving the platelets; however, it is preferred to store platelets in a concentrate which comprises povidone, with or without a sterilizing component or reagent, and thereafter to reconstitute the platelets in plasma or saline.

It is highly preferable to use a povidone-enriched povidone-iodine; indeed, the invention can be carried out satisfactorily for some purposes using povidone and another antiviral or antibiotic material. such GTPD compounds, or providing other sterilization.

Pathogenic microbes in platelet-containing products can be eliminated, without interference with other treatment and processing procedures, by adding molecular iodine, e.g. povidone-$I_2$, to pooled plasma, preferably early in the process of collecting and pooling the plasma, or as a terminal sterilization and storage step.

The above applications in which the platelets, carried in a liquid, can be carried out by flowing the liquid through a bed of solid particles of povidone-iodine of suitable size or by contacting the liquid and/or the cells in the liquid with particles or a membrane or surface of solid povidone-iodine. Where a bed of particles is used with a cell-bearing liquid, the particles must be large enough to permit intimate contact without acting as a filter, i.e. entrapping or binding the cells. The platelets can be protected by providing from 0.1 to 10 percent povidone iodine having a molecular weight of under about 40,000 and preferably under 20,000 daltons. It has been found that these low molecular weight povidones have a very striking effect on the life and characteristics of platelets. It is very difficult to measure the effect of storage on platelets, beyond their gross destruction, however, it is well-known that platelet compositions have a very limited storage life. The use of these relatively low molecular weight povidone compounds greatly increases the storage life of platelet concentrates. If platelets are stored in a relatively low molecular weight ($<\sim$40 kD) povidone solution containing at least about 0.1% (by weight) povidone, either as povidone per se or povidone-iodine or povidone-hydrogen peroxide (available from GAF), or a combination of these, and then resuspended in plasma, aggregation and clot retraction returns toward normal.

Polyvinyl pyrrolidone used in the preparation of soluble povidone-iodine preparations is polymerized to a molecular weight of from about 10 Kdaltons to 40 Kdaltons, 30 Kdaltons being a typical molecular weight. However, povidone-iodine preparations can be prepared using very much higher molecular weight polymers which only tend to swell rather than to dissolve in aqueous solutions. It is the use of these higher molecular weight Polyvinyl pyrrolidone polymers reacted with $I_2$ to form solid, substantially water insoluble povidone-iodine compositions that the present invention is directed.

Maximum platelet protection is obtained using povidone under 40 kD molecular weight, maximum protection being obtained using povidone of about 15 kD.

In carrying out this invention, the platelet-containing liquid, preferably protect by povidone in solution, may be contacted with the solid povidone-iodine. This may be done most efficiently, in most cases, by passing the liquid through a settled or fluidized or bed of povidone-iodine particles on a large pore filter or support. The platelet concentrate may be treated by mixing the particles in a container of the liquid or passing the liquid over a surface of the povidone-iodine material, e.g. over a multiple-plate array of sheets of such material. The povidone-iodine may be washed and the $I_2$ content therein regenerated between uses.

The biological destruction of blood factors following infusion into the patient is a well-known phenomena. Factor VIII, which is one of the more widely used blood factors, has a short biological half-life (the time period in which one-half of the starting concentration disappears) of a few hours. The half-life of all blood factors is so short that frequent infusions are required. It would be a major step forward if the half-life of blood factors could be significantly extended. The extremely high cost of blood factors and medical services required for infusing the patient and the pain and discomfort of the patient could be greatly reduced, while, at the same time, providing the patient with a more consistent level of the particular blood factor(s) required. It is an object of this invention to accomplish the result in a safe and economical manner.

This invention is embodied in a method of treating patients with blood factors, e.g. Factor VIII or Anti-Hemophilia Factor (AHF), to increase the biological half-life of such factors in therapy, and to compositions of factors and methods of preparing the same.

Blood factors concentrates and compositions are treated following separation from interfering proteins by the addition of povidone and/or albumin, preferably biological competent albumin prepared by the process described in my co-pending patent application BIOLOGICALLY COMPETENT PURIFIED ALBUMIN. Such compositions consist essentially of the respective blood factor(s) and either povidone or albumin, or both, in an suitable carrier solution which may contain buffers, preservatives, etc., and may contain povidone-iodine complex. If povidone-iodine complex is present, the ratio of povidone to iodine is at least about 12 to 1, preferably at least 15 to 1. Povidone-iodine may be present in a concentration of from about 0.05$^w$/o to about 5$^2$/w povidone-iodine.

Povidone or albumin, or mixtures of both, are mixed with the particular blood factor being prepared or to be infused. The addition can be during preparation, after interfering proteins have been removed, or immediately before infusion into the patient, or at any intermediate time. Povidone and/or albumin are added to comprise from 0.05 to 5 weight percent of the final aqueous infusion solution. Povidone-iodine complex, with excess povidone such that the ratio of povidone to iodine is at least about 12 to 1, is a desirable additive. It is believed that blood factors are coupled through the iodine, or that binding of the blood factor to the povidone is enhanced by iodine giving a stable, longer half-life blood factor product. The biological mechanism involved is not known for certain, but it is believed that the blood factor couples with or complexes with the povidone or albumin and is protected against biological destruction. The blood factors are apparently released over a period of time and circulate in the blood performing their particular function. It appears that the destruction of the blood factors is a function of the concentration of the free blood factor in the blood. By protecting substantial portions of the blood factor by coupling it with large molecules such as albumin and/or povidone, the rate of destruction is reduced. It is believed that a quasi-equilibrium exists between the concentration of free blood factor and the amount of bound blood factor resulting in a replenishment of free blood factor over a period of time. In any event, a very substantial increase in effective half-life of blood factors in the patient may be achieved. The effective half-life is believed to be extended by a factor of three to six or more.

Blood transfusion and infusion methods and methods and equipment for the infusion of blood factors into patients are generally known and commonly used in medicine and no special equipment or techniques, beyond those described, are required.

The method of treating patients comprises infusing into the blood stream of the patient an aqueous solution consisting essentially of one or more blood factors and povidone or albumin or a mixture of povidone or albumin and optionally povidone-iodine complex wherein the ratio of povidone to iodine is at least about 12 to 1, preferably 15:1 to 60:1.

A composition suitable for use in this invention consists essentially of one or more human blood factors free from significant quantities of blood plasma and povidone or albumin or a mixture of povidone and albumin and optionally povidone-iodine complex wherein the ratio of povidone to iodine is at least about 12 to 1, preferably 15:1 to 60:1.

A method of preparing human blood factors for infusion into a patient comprising mixing one or more blood factors that are substantially free from blood plasma with one or more blood factors and povidone or albumin or a mixture of povidone or albumin and optionally with povidone-iodine complex wherein the ratio of povidone to iodine is at least about 12 to 1. preferably 15:1 to 60:1, is also disclosed as a part of this invention.

Industrial Application

This invention finds application in medicine and veterinary science.

What is claimed is:

1. A method of treating patients to prevent the transmission of microbial infectious disease comprising infusing into the patient platelet concentrate that has been in contact with povidone-iodine or povidone-hydrogen peroxide, or a mixture of povidone-iodine and povidone-hydrogen peroxide in a concentration of from 0.001 to 0.5 weight percent for at least one-half minute to inactivate or destroy infectious microbes therein.

2. The method of protecting platelets comprising storing said platelets in a solution comprising from at least about 0.1 weight percent povidone and thereafter reconstituting the platelets in plasma for infusion into a patient.

3. The method of claim 2 wherein the solution comprises at least 0.1 weight percent povidone iodine, at least half of the povidone therein having a molecular weight of less than about 40 kD.

4. The method of claim 2 wherein the solution further comprises povidone hydrogen peroxide.

5. The method of purifying platelet-bearing liquid comprising the steps of:
   contacting the liquid to be purified into contact with solid povidone-iodine to expose the liquid to $I_2$ on such surface to kill pathogenic organisms therein; and
   removing the liquid from contact with the solid povidone-iodine.

6. The method of claim 6 further comprising the step of reacting the surface of the solid povidone-iodine to regenerate the iodine content thereof.

7. A therapeutic composition of matter consisting essentially of platelet concentrate comprising at least about 0.1 weight percent povidone having a molecular weight of under about 40 kD.

8. The method of treating patients comprising infusing into the blood stream of the patient an aqueous solution consisting essentially of one or more blood factors and povidone or albumin or a mixture of povidone or albumin and optionally povidone-iodine complex wherein the ratio of povidone to iodine is at least about 15 to 1.

9. A composition consisting essentially of:
   (a) one or more human blood factors free from blood plasma and
   (b) povidone or albumin or a mixture of povidone and albumin and optionally povidone-iodine complex wherein the ratio of povidone to iodine is at least about 15 to 1.

10. A method of preparing human blood factors for infusion into a patient comprising mixing one or more blood factors that are substantially free from blood plasma with one or more blood factors and povidone or albumin or a mixture of povidone or albumin and optionally with povidone-iodine complex wherein the ratio of povidone to iodine is at least about 15 to 1.

* * * * *